United States Patent [19]

Wang et al.

[11] Patent Number: 5,110,809

[45] Date of Patent: May 5, 1992

[54] ANTIFUNGAL GEL FORMULATIONS

[75] Inventors: Jonas Wang, Robbinsville, N.J.; Bhiku Patel, Amherst, N.Y.; Stacley Au, Tonawanda, N.Y.; Hemanshu Shah, Williamsville, N.Y.

[73] Assignee: Bristol-Myers Squibb Company, New York, N.Y.

[21] Appl. No.: 601,958

[22] Filed: Oct. 23, 1990

Related U.S. Application Data

[60] Division of Ser. No. 323,727, Mar. 15, 1989, Pat. No. 5,002,938, which is a continuation-in-part of Ser. No. 381,059, Mar. 7, 1989, abandoned, which is a continuation of Ser. No. 171,350, Mar. 21, 1988, abandoned.

[51] Int. Cl.$^5$ .............. A61K 9/06; A61K 31/415; A61K 31/57

[52] U.S. Cl. .................... 514/171; 514/179; 514/399; 514/781; 514/944

[58] Field of Search .............. 514/171, 179, 399, 781, 514/944

[56] References Cited

U.S. PATENT DOCUMENTS

| | | | |
|---|---|---|---|
| 3,749,773 | 7/1973 | Ninger et al. | 514/179 |
| 3,856,954 | 12/1974 | Jackson | 514/944 |
| 3,899,580 | 8/1975 | O'Neill et al. | 514/179 |
| 3,949,072 | 4/1976 | Tenta | 514/164 |
| 4,013,792 | 3/1977 | Eichman et al. | 514/944 |
| 4,082,881 | 4/1978 | Chen et al. | 514/171 |
| 4,112,121 | 9/1978 | Tenta | 514/731 |
| 4,242,359 | 12/1980 | Cooper et al. | 514/663 |
| 4,244,942 | 1/1981 | Kamishita et al. | 514/179 |
| 4,246,261 | 1/1981 | Van Scott et al. | 514/171 |
| 4,247,547 | 1/1981 | Marks | 424/81 |
| 4,267,169 | 5/1981 | Kamishita et al. | 514/396 |
| 4,267,173 | 5/1981 | Draper | 514/179 |
| 4,323,558 | 4/1982 | Nelson | 514/887 |
| 4,393,076 | 7/1983 | Noda et al. | 424/499 |
| 4,457,938 | 7/1984 | von Bittura et al. | 514/396 |
| 4,472,376 | 9/1984 | Kamishita | 514/944 |
| 4,478,822 | 10/1984 | Haslam et al. | 514/179 |
| 4,576,936 | 3/1986 | MacDonald | 514/180 |
| 4,604,384 | 8/1986 | Smith et al. | 514/179 |
| 4,636,520 | 1/1987 | Umio et al. | 514/427 |
| 4,654,209 | 3/1987 | Leslie et al. | 514/179 |
| 4,767,751 | 8/1988 | Davis | 514/179 |
| 4,803,066 | 2/1989 | Edwards | 514/969 |
| 4,843,096 | 6/1989 | Stiefel | 514/559 |
| 4,844,902 | 7/1989 | Grohe | 424/449 |
| 4,866,050 | 9/1989 | Ben-Amuz | 514/179 |
| 4,867,970 | 9/1989 | Newsham et al. | 424/81 |
| 4,868,169 | 9/1989 | O'Laughlin et al. | 514/179 |
| 4,868,170 | 9/1989 | Faustino et al. | 514/179 |
| 4,897,260 | 1/1990 | Ross et al. | 514/944 |
| 4,948,580 | 8/1990 | Browning | 514/944 |
| 5,002,938 | 3/1991 | Wang et al. | 514/171 |

FOREIGN PATENT DOCUMENTS

| | | | |
|---|---|---|---|
| 0186055 | 7/1986 | European Pat. Off. | 514/944 |
| 0061518 | 4/1985 | Japan | 514/944 |

OTHER PUBLICATIONS

Wortzel, M. Y., H., A Double-Blind Study Comparing the Superiority of a Combination Anti-Fungal (Clotrimazole/Steroidal(Betamethasone Dipropionate)) Product, Cutis 30:258 (1982).

Katz, H. I., Bard, J., Cole, G. W., Fischer, S., McCormick, G. E., Medansky, R. S., Nesbitt, L. T., and Rex, I. H., SCH 370 (Clotrimazole-Betamethasone Dipropionate) Cream in Patients with Tinea Cruri or Tinea Corporis. Cutis, 34(2), 183-8 (1984).

Bruice, T. C., and Schmir, G. L., Arch. Biochem. Biophys. 63:484 (1956).

Bruice, T. C., and Schmir, G. L., Imidazole Catalysis. I. The Catalysis of the Hydrolysis of Phenyl Acetates by Imidazole, J. Am. Chem. Soc., 79:1663-9 (1957).

Bruice, T. C., and Schmir, G. L., Imidazole Catalysis. II. The Reaction of Substituted Imidazoles with Phenyl Acetates in Aqueous Solution., J. Am. Chem. Soc., 80:148-56 (1958).

(List continued on next page.)

Primary Examiner—Shep K. Rose
Attorney, Agent, or Firm—Sandra M. Nolan

[57] ABSTRACT

Stable anhydrous gel formulations for topical antifungal use contain an imidazole, a steroid, a co-solvent system comprising monohydric and dihydric alcohols, and a hydroxyalkylcellulose gellant.

8 Claims, 2 Drawing Sheets

OTHER PUBLICATIONS

Bender, M. L., and Turnquest, B. W., General Basic Catalysis of Ester Hydrolysis and Its Relationship to Enzymatic Hydrolysis, J. Am. Chem. Soc., 79:1656-62 (1957).

Richter Gedeon Vegy, Stable Antifungal and Anti-Inflammatory Ointment, UK 1,474,510.

Yip, Y. W., Po, L. W., and Irwin, W. J., Kinetics of Decomposition and Formulation of Hydrocortisone Butyrate in Semi-Aqueous and Gel Systems, J. Pharm. Sci., 72, 776-81 (1983).

Gupta, V. D., Effect of Vehicles and Other Active Ingredients on Stability of Hydrocortisone., J. Pharm. Sci., 67:299 (1978).

Hansen, J. and Bundgaard, H., Studies on the Stability of Corticosteroids V. The Degradation Pattern of Hydrocortisone in Aqueous Solution., Int. J. Pharm., 6:307-19 (1980).

Von Bittera et al., CA 101:116738e (1984) of Ger. Offen DE 3243546, May 30, 1984.

Hisamatsu[II], CA 103:92854c (1985) of Jpn. Kokai JP 60/61518, Apr. 9, 1985.

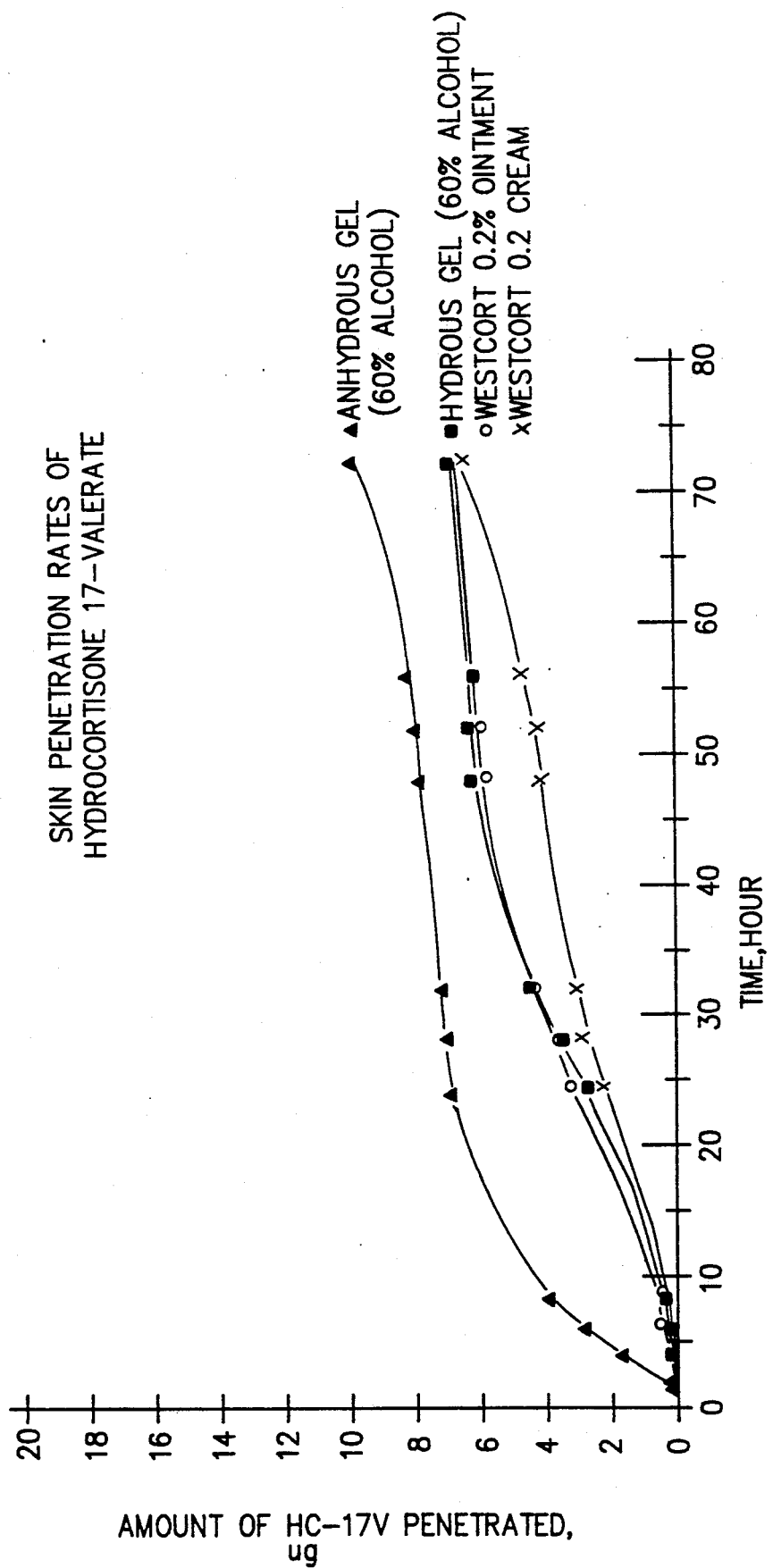

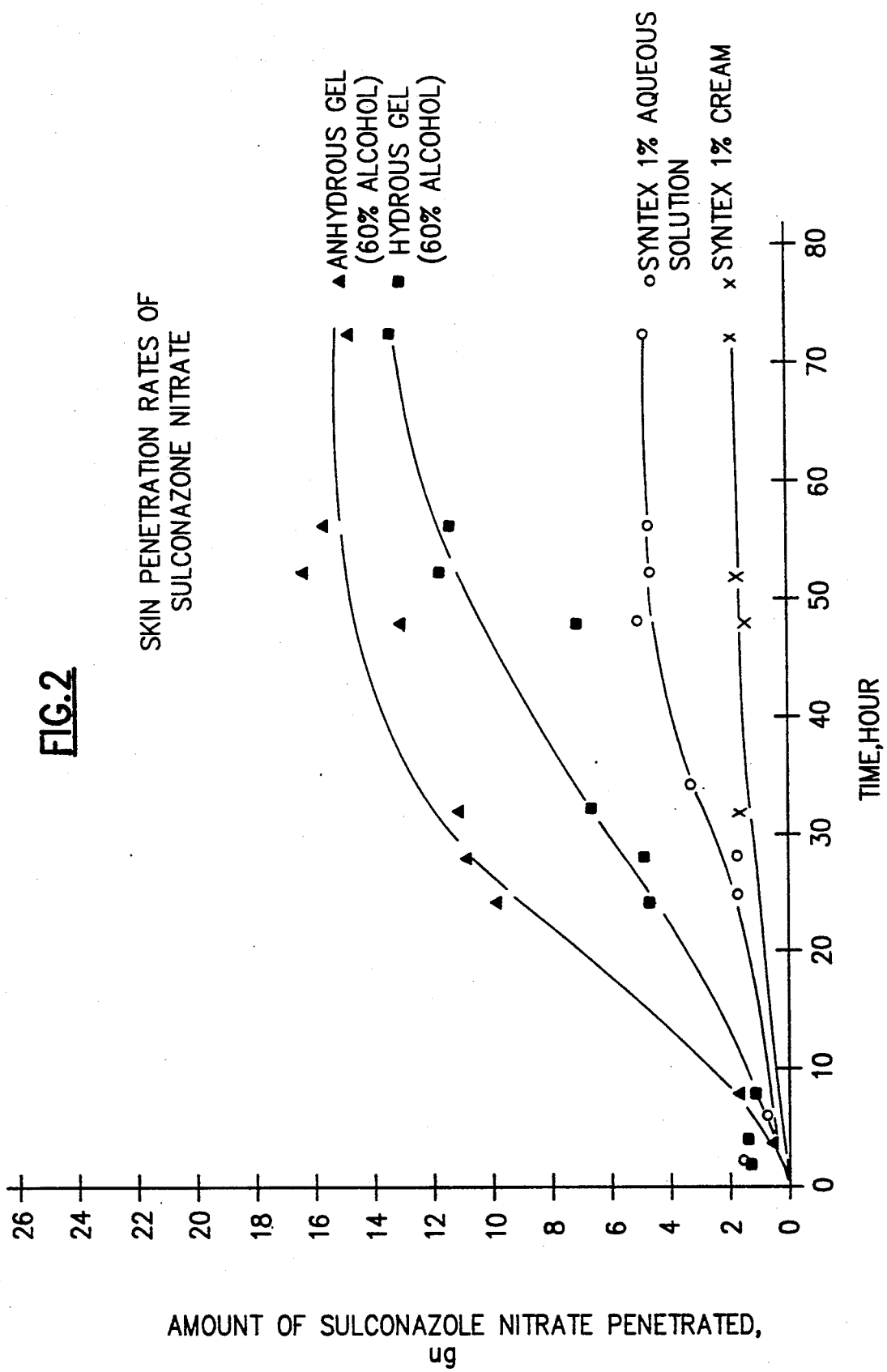

ANTIFUNGAL GEL FORMULATIONS

CROSS-REFERENCE TO RELATED APPLICATION

This application is a division of Ser. No. 323,727, filed Mar. 15, 1989, now U.S. Pat. No. 5,002,938, which was a continuation-in-part of Ser. No. 381,059, filed Mar. 7, 1989 and now abandoned which was a continuation of Ser. No. 171,350, filed Mar. 21, 1988 and now abandoned.

BACKGROUND OF THE INVENTION

The present invention relates to a stable gel formulation for the topical application of a combination of an imidazole antifungal agent and a 17-ester steroid antiinflammatory agent. The product is particularly suitable for treating fungal diseases such as tinea capitis, tinea corporis or tinea cruris. Decomposition of the 17-ester steroid resulting from interaction with water and the imidazole antifungal agent during storage is drastically reduced by the present gel formulation.

A fungus is a very small microscopic type of plant cell which may grow on the skin and, under certain conditions, produce an infection. Such infections caused by fungi, the mycoses, are among the oldest known to man and have long been recognized as a highly prevalent public health problem. When the fungus infection involves the scalp, it is known as tinea capitis; when it involves the feet it is known as tinea pedis (athlete's foot); when it occurs on the body it is known as tinea corporis; and when it occurs in the groin it is known as tinea cruris.

A variety of methods have been used for the treatment of fungal infections including the use of potassium iodide, Whitfield's ointment, undecylenic acid, antibiotics (e.g. nystatin and amphotericin B), griseofulvin and the imidazole antifungal agents such as miconazole, clotrimazole, econazole and sulconazole.

Although the systemic administration of antibiotics such as nystatin and amphotericin B has been used with some success, the low bioavailability and systemic toxicity of these agents have restricted their use in treating mycotic infections.

The imidazoles are the first broad-spectrum antifungals and are of considerable importance in clinical practice. Their broad spectrum of antifungal activity, extending to most pathogenic fungi, has provided an important advance in antifungal therapy.

As used herein the term "imidazole antifungal agent" means any agent having an imidazole functional group in the molecule and possessing topical antifungal activity. A large number of suitable imidazoles have been described in the literature and are well-known to those skilled in the art. Examples of suitable imidazole antifungal agents include sulconazole nitrate, econazole nitrate, miconazole nitrate and clotrimazole.

The fungal infections are commonly associated with signs of erythema and scaling and with symptoms of itching or painful burning. Clinical treatment for fungal disease requires at least two to four weeks for complete relief of symptoms. More recently, it has been found that fungal infections can be effectively treated with a combination product containing corticosteroids and imidazole antifungal agents. It is known that the sensitivity of fungal organisms varies with their life cycles; spores are more resistant to treatment than are mycelia. Steroids may induce fungal spores to produce mycelia, thereby making them more sensitive to treatment. Also, steroids are known to produce vasoconstriction at the site of application. This activity may delay or prevent the elimination of the antifungal agent from the application site, permitting the antifungal agent to remain in the epidermis for longer periods of time. It is therefore believed that a locally applied antiinflammatory agent would offer direct and immediate relief for the inflammatory component of the lesion. The combination product should then provide fast relief of symptoms and eradicate the infection. Based on this concept, certain combinations of an antifungal agent and an antiinflammatory agent have recently been developed for treatment of fungal disease. Currently, the commercially available combination products using this concept are Lotrisone cream (clotrimazole 1%/betamethasone dipropionate 0.05%), Daktacort cream (miconazole nitrate 2%/hydrocortisone 1%) and Canesten HC cream (clotrimazole 1%/hydrocortisone 1%).

Katz and other dermatologists[1,2] found that Lotrisone cream was therapeutically and mycologically better than clotrimazole 1% and betamethasone dipropionate 0.05% alone. Notwithstanding its clinical advantages, Lotrisone cream possesses some undesirable attributes. It contains a rather strong fluorinated steroid, betamethasone dipropionate, which can be quite cosmetically dangerous to use in intertrigious regions. Other undesirable attributes include skin atrophy, rebound phenomenon and telengiectasia.

Other marketed combination products of this type, e.g. Daktacort cream and Canesten HC cream, are combinations of low-potency steroids and imidazoles. Such combination products always fail to provide the fast relief of the inflammatory symptoms which is normally desired for the treatment of a fungal infection.

A combination of a non-halogenated mid-potency steroid and an imidazole antifungal agent would appear to be an ideal choice for the topical treatment of fungal disease. It was the object of the present invention to develop such a combination product.

The mid-potency steroid used in the combination product of the present invention is a 17-ester steroid which possesses enhanced activity relative to the parent alcohol but fewer undesirable side effects than the halogenated steroids which are comparable in activity. Examples of 17-ester corticosteroids included within the scope of the invention are hydrocortisone 17-acetate, hydrocortisone 17-butyrate, hydrocortisone 17-valerate, hydrocortisone 17-propionate, betamethasone 17-valerate, cortisone 17-acetate, prednisone 17-acetate and prednisone 17-valerate.

The 17-ester steroids per se have excellent stability in conventional topical dosage forms. In our studies topical dosage forms are tested for stability by determining their $t_{90\%}$ values where $t_{90\%}$ is the time in days required for a dosage form to lose 10% of its chemical and/or biological activity. A 0.2% hydrocortisone 17-valerate o/w cream in this test had a $t_{90\%}$ of 536 days at room temperature (25° C.±2° C.). Use of a standard 10% overage of active ingredient in the cream would mean that such a product would have an acceptable shelf life (time required for potency to decrease to 90% of label strength) at room temperature of 1072 days or more than 2.9 years.

A cream formulation is generally more acceptable to a patient than other topical dosage forms, e.g. liquid, petrolatum ointment, oil, etc., from the point of view of aesthetics and ease of application. Unfortunately, when one attempts to combine a 17-ester steroid and an imidazole antifungal agent to make a combination product as described above, the stability of the 17-ester steroid is drastically reduced to unacceptable levels in almost all conventional cream formulations. To develop a cream vehicle for a combination product of a 17-ester steroid and an imidazole, we have prepared for stability evaluation more than 60 different types of cream vehicles including o/w creams, w/o creams, creams with high or low petrolatum content, with low or high surfactant content, with high or low water content, and with different propylene glycol content. Almost all creams failed our stability test, either due to the chemical instability of the 17-ester steroids or the physical separation of emulsion caused by the salting effect of the imidazole salt when used in concentrations of about 1% or more. Cream formulations often necessitate the use of emulsifiers or surfactants to maintain their physical stability and the use of antimicrobial preservatives to prevent microbiological contamination. These additives tend to generate an undesirable environment which can accelerate the hydrolysis of 17-ester steroids and the physical separation due to the salting out. In addition, it is known that imidazoles can also be catalysts for the hydrolysis of esters[3-7]. Such degradation was in fact observed in our preliminary studies (see Table I below).

TABLE 1

Degradation rates of hydrocortisone 17-valerates (HC 17-V) in the presence of 1% imidazoles in various topical creams at 25° C. ± 2.0° C.

| Formulations | k, day$^{-1}$**** | t$_{90\%}$, days*** |
|---|---|---|
| 1. Sulconazole nitrate 1%/ HC 17-V 0.2% in aqueous-alcohol solution at pH 4.7 | $3.07 \times 10^{-3}$ | 34 |
| 2. Sulconazole nitrate 1%/ HC 17-v 0.2% in o/w cream at pH 4.7 | $5.96 \times 10^{-3}$ | 18 |
| 3. Sulconazole nitrate 1%/ HC 17-V 0.5% in USP XXI Oint. at 4.7 | $7.40 \times 10^{-3}$ | 14 |
| 4. Sulconazole nitrate 1%/ HC 17-V 0.2% in Carbapol* gel | $6.50 \times 10^{-3}$ | 16 |
| 5. Sulconazole nitrate 1%/ HC 17-V 0.2% in Methocel** gel | physical separation | |
| 6. Sulconazole nitrate 1%/ HC 17-V 0.2% in pure petrolatum base | $2.24 \times 10^{-3}$ | 47 |
| 7. Econazole nitrate 1%/ HC 17-V 0.2% in USP XXI hydrophilic ointment | $1.34 \times 10^{-2}$ | 7.8 |
| 8. Miconazole nitrate 1%/ HC 17-V 0.2% in o/w cream | $2.99 \times 10^{-2}$ | 3.5 |
| 9. Miconazole nitrate 1%/ HC 17-V 0.2% in USP XXI hydrophilic ointment | $4.28 \times 10^{-2}$ | 2.5 |
| 10. Clotrimazole 1%/HC 17-V 0.2% in o/w cream | $4.39 \times 10^{-3}$ | 24 |
| 11. Clotrimazole 1%/HC 17-V 0.2% in USP XXI hydrophilic ointment | $2.26 \times 10^{-2}$ | 4.6 |

*Carbopol gel is a carboxy vinyl polymer of high molecular weight (CTFA names: carbomer-934p, -940, -961)
**Methocel gel is the methyl ether of cellulose (CTFA name: methylcellulose, trade names: Methocel MC, Cellulose Methyl Ether).
***t$_{90\%}$ = time required for hydrocortisone 17-valerate activity to be reduced to 90% of original
****k = degradation rate of hydrocortisone 17-valerate component Based on our studies it is believed that the necessity of using emulsifiers or surfactants in most cream formulations results in increased interaction of the 17-ester steroid with water and imidazole molecules, thereby causing rapid hydrolysis of the 17-ester steroid (see Table I, formulations 2, 3 and 7–11).

Several commonly used gel formulations prepared without any emulsifier or surfactant and with a gelling agent selected from a group consisting of an acidic carboxy polymer, such as those available under the trade names Carbopol 934, Carbopol 940, and a methyl ether of cellulose available under the trade name Methocel MC, were used for combination products. As shown in Table I, formulations 4 and 5, a fast degradation at the carbon-17 position of the 17-ester steroids was still observed.

Moreover, in a subsequent experiment, a mixture of an imidazole with hydrocortisone 17-valerate also showed rapid hydrolysis even in pure petrolatum. Poor dispersibility is considered the cause of the stability failure in the pure petrolatum system (see Table I, formulation 6).

Since ester hydrolysis is known to be affected by pH, the stability of an imidazole with a 17-ester steroid o/w cream system adjusted to different pHs was studied. The results (Table II) show that simple pH adjustment will not impart the required stability.

TABLE II

Degradation rates of hydrocortisone 17-valerate 0.2% in the presence of 1% sulconazole nitrate in USP XXI hydrophilic ointment (an o/w cream) at 25° C. ± 2.0° C. at different pH.

| pH | k, day$^{-1}$ | t$_{90\%}$, days |
|---|---|---|
| 2.10 | $2.10 \times 10^{-3}$ | 50 |
| 4.00 | $3.80 \times 10^{-3}$ | 28 |
| 4.70 | $4.45 \times 10^{-3}$ | 24 |
| 6.50 | $5.20 \times 10^{-3}$ | 20 |

In order to prevent the degradation of hydrocortisone and its derivatives in topical formulations, it has been proposed to use the steroid active ingredient in association with certain stabilizers (e.g. EDTA, antioxidants) or to reduce the amount of propylene glycol used in the formulation [8-10]. Despite using stabilizers or reducing the concentration of propylene glycol in the steroid formulations of the prior art, it has not been possible to obtain topical solutions, gels or creams of a combination product having acceptable (two years or more) long term stability.

To fulfill the unmet needs, it remained highly desirable to obtain a combination of an imidazole antifungal agent and a 17-ester antiinflammatory corticosteroid in a topical dosage form which would be stable for at least two years at room temperature (25°±2° C.). It was an object of the present invention to provide such a stable combination product from which the imidazole and 17-ester steroid would be readily available for absorption by the skin. It was also an object to provide a combination product formulation which could be applied to the affected skin, e.g. the intertrigious area, without flowing onto the healthy parts of the skin. This latter property would minimize the undesirable side effects that might be caused by absorption through surrounding tissue. Such a combination product then, would not only provide fast relief of symptoms and the eradication of the fungal infection but would also minimize the risk of undesirable side effects.

It was a further object of the present invention to provide a topical antifungal treatment which can effectively provide fast relief of symptoms and eradication of the fungal infection while minimizing the risk of undesirable side effects caused by high-potency and/or fluorinated steroids.

It was another object of the invention to provide topical gel formulations of mid-potency 17-ester steroids and imidazole antifungal agents which possess good dispersibility and good physical and chemical stability without refrigeration and without the need for special additives such as emulsifiers or surfactants or antimicrobial preservatives.

It was another object of the invention to provide topical gel formulations of 17-ester steroids and imidazoles having other desirable qualities such as being cosmetically acceptable and allowing accurate application of effective amounts of the two active ingredients to the desired lesion.

It was still another object of the invention to provide topical gel formulations which enhance delivery of a 17-ester steroid and imidazole to their respective target sites, thereby ensuring that a maximum therapeutic advantage could be achieved.

These and other objects of the present invention will be more fully understood in the light of the specific examples and description set forth below.

SUMMARY OF THE INVENTION

The present invention provides a stable gel formulation for topical administration comprising a therapeutically effective amount of a mixture of an imidazole antifungal agent and a 17-ester steroid antiinflammatory agent in a vehicle system comprising (a) a co-solvent system for the imidazole and 17-ester steroid consisting essentially of a lower alkanol in combination with a dihydroxy alcohol or a trihydroxy alcohol, or a mixture thereof and (b) an effective amount to cause gelling of hydroxypropyl cellulose or hydroxyethyl cellulose. Such gel formulation may contain 0 to 20% (by weight) water.

BRIEF DESCRIPTION OF THE DRAWINGS

FIG. 1 represents a comparison of the skin penetration rates of hydrocortisone 17-valerate in aqueous and anhydrous gel formulations of the present invention with the rates in hydrocortisone 17-valerate cream and ointment formulations. FIG. 2 represents a comparison of the skin penetration rates of sulconazone nitrate in aqueous and anhydrous gel formulations of the present invention with the rates in sulconazone nitrate creams and aqueous solutions.

DETAILED DESCRIPTION

It was discovered during experiments carried out by the present inventors that the stability of formulations containing both imidazoles and 17-ester steroids seemed to be dependent on dispersibility. For example, in cream or solution formulations, the stability improved as the concentration of water in the formulation decreased. Also, viscous creams or pure petrolatum bases did not provide good stability. Thus, only cream formulations with higher solvency of the 17-ester steroid and imidazole can provide satisfactory stability due to their better dispersibility which reduces the interaction of these two agents.

Imidazoles are insoluble in most common aqueous and non-aqueous solvents including water. They can be solubilized in aqueous vehicles only if the vehicles contain high concentrations of surfactants (greater than 10%). With high surfactant concentration, however, 17-ester steroids are subject to rapid hydrolysis.

It has been discovered by the present inventors that the only vehicles in which 17-ester steroids and imidazoles are soluble, evenly dispersed and stable are certain organic solvents. More particularly, the two active components must be dissolved in a co-solvent system consisting essentially of a lower alkanol in combination with a dihydroxy alcohol or trihydroxy alcohol or mixtures thereof. Examples of suitable dihydroxy alcohols are hexanediols such as 2-ethyl-1,3-hexanediol and glycols such as ethylene glycol, propylene glycol and 1,3-butylene glycol. The most preferred glycol is propylene glycol. Examples of trihydroxy alcohol are hexanetriols such as 1,2,6-hexanetriol. Lower alkanols include such alcohols as methanol, ethanol, propanol, isopropanol, butanol, and the like. The most preferred lower alkanols are isopropanol and ethanol, or mixtures thereof. Preferably, the dihydroxy alcohol is present in an amount of 0 to 45% by weight and/or trihydroxy alcohol is present in an amount of from about 0 to 40% by weight and the lower alkanol in an amount of from about 30–65% by weight. The skin penetration rates of imidazole and steroid can be adjusted by varying the concentrations of co-solvent system in the formulation. Higher concentrations of alcohol give a higher depot effect and an enhanced skin penetration rate. However, higher alcohol concentrations also increase skin irritation with concentrations over about 60% by weight resulting in excessive irritation. Therefore, a balance has to be maintained between a desire to enhance skin penetration rates of the active components, particularly the imidazole component, and a desire to achieve a non-irritating product.

As indicated in Table III, the formulations of the present invention enhance the stability of 17-ester steroids almost 5-40 times in terms of $t_{90\%}$. The substantial stability enhancement seen here is in startling contrast to the instability found in other cream and gel formulations. With 10% overage of 17-ester steroid, the stability profile for the formulations of the present invention supports a 2 year expiration dating period at room temperature. All $t_{90\%}$ values given in Table III below were determined at 25° C. ±2° C.

TABLE III

Degradation rates of 17-ester hydrocortisone in the presence of 1% imidazoles in the present invention gel formulations at 25° C. ± 2.0° C.

(1) R&D Product No. 30159-B-19-A(FN7-969-06)

| Ingredient | % w/w |
| --- | --- |
| Sulconazole nitrate | 1% |
| Hydrocortisone 17-valerate | 0.2% |
| SD Alcohol 40 | 50% |
| Propylene glycol | 30% |
| PPG-5-Ceteth-20 | 12.3% |
| Isopropyl myristate | 5% |
| Hydroxypropyl cellulose | 0.9% |
| Salicylic acid | 0.5% |
| Ascorbyl palmitate | 0.1% |

| FN7-969-06 | k, day$^{-1}$ | $t_{90\%}$, days |
| --- | --- | --- |
| Chemical Stability result | 2.39 × 10$^{-4}$ | 440 |

(2) R&D Product No. 30159-B-23-A(FN7-994-02)

| Ingredient | % w/w |
| --- | --- |
| Sulconazole nitrate | 1% |
| Hydrocortisone 17-valerate | 0.2% |
| SD Alcohol 40 | 35% |
| Propylene glycol | 40% |
| PPG-5-Ceteth-20 | 12.3% |
| Water for production | 5% |
| Isopropyl myristate | 5% |
| Hydroxypropyl cellulose | 0.9% |

TABLE III-continued

Degradation rates of 17-ester hydrocortisone in the presence of 1% imidazoles in the present invention gel formulations at 25° C. ± 2.0° C.

| | |
|---|---|
| Salicylic acid | 0.5% |
| Ascorbyl palmitate | 0.1% |

| FN7-994-02 | k, day$^{-1}$ | t$_{90\%}$, days |
|---|---|---|
| Chemical Stability result | 2.20 × 10$^{-4}$ | 477 |

(3) (FN7-944-18)

| Ingredient | % w/w |
|---|---|
| Miconazole nitrate | 1% |
| Hydrocortisone 17-valerate | 0.2% |
| SD Alcohol 40 | 50% |
| Propylene glycol | 30% |
| PPG-5-Ceteth-20 | 12.45% |
| Isopropyl myristate | 5% |
| Hydroxypropyl cellulose | 0.75% |
| Salicylic acid | 0.5% |
| Ascorbyl palmitate | 0.1% |

| FN7-994-18 | k, day$^{-1}$ | t$_{90\%}$, days |
|---|---|---|
| Chemical Stability result | 2.08 × 10$^{-4}$ | 506 |

(4) (FN7-944-19)

| Ingredient | % w/w |
|---|---|
| Econazole nitrate | 1% |
| Hydrocortisone 17-valerate | 0.2% |
| SD Alcohol 40 | 50% |
| Propylene glycol | 30% |
| PPG-5-Ceteth-20 | 12.45% |
| Isopropyl myristate | 5% |
| Hydroxypropyl cellulose | 0.75% |
| Salicylic acid | 0.5% |
| Ascorbyl palmitate | 0.1% |

| FN7-994-19 | k, day$^{-1}$ | t$_{90\%}$, days |
|---|---|---|
| Chemical Stability result | 3.33 × 10$^{-4}$ | 316 |

(5) (FN7-944-20)

| Ingredient | % w/w |
|---|---|
| Clotrimazole | 1% |
| Hydrocortisone 17-valerate | 0.2% |
| SD Alcohol 40 | 50% |
| Propylene glycol | 30% |
| PPG-5-Ceteth-20 | 12.45% |
| Isopropyl myristate | 5% |
| Hydroxypropyl cellulose | 0.75% |
| Salicylic acid | 0.5% |
| Ascorbyl palmitate | 0.1% |

| FN7-944-20 | k, day$^{-1}$ | t$_{90\%}$, days |
|---|---|---|
| Chemical Stability result | 2.42 × 10$^{-4}$ | 434 |

(6) (FN8-1094-20)

| Ingredient | % w/w |
|---|---|
| Sulconazole nitrate | 1% |
| Hydrocortisone 17-valerate | 0.2% |
| SD Alcohol 40 | 50% |
| 2-Ethyl-1,3-Hexanediol | 22% |
| 1,2,6-Hexanetriol | 15% |
| Isopropyl myristate | 5% |
| Water | 4.99% |
| Hydroxypropyl cellulose | 0.9% |
| Salicylic acid | 0.5% |
| BHT | 0.2% |
| BHA | 0.2% |
| Disodium EDTA | 0.01% |
| Q.S. NaOH 1N adjust pH to 4.0 | |

| FN8-1094-20 | k, day$^{-1}$ | t$_{90\%}$, days |
|---|---|---|
| Chemical Stability result | 3.33 × 10$^{-4}$ | 316 |

In addition to the two active components and the co-solvent system, there is also required in the present gel formulations an effective amount to cause gelling of either hydroxypropyl cellulose or hydroxyethyl cellulose. As noted previously, other gelling agents such as methyl cellulose and carboxy vinyl polymer gels gave unstable gel formulations. Generally the gelling agent will be present in an amount of from about 0.1 to 5%.

A general formula encompassing gel formulations within the scope of the present invention is set forth below. All amounts are in weight percent.

General Gel Formula in % w/w

| Component | Amount, % w/w |
|---|---|
| Imidazole antifungal agent | 0.2–2.0 |
| 17-Ester steroid | 0.01–2.5 |
| Lower alkanol | 30–60 |
| Dihydroxy alcohol | 0–45 |
| Trihydroxy alcohol | 0–40 |
| Gelling agent | 0.1–5 |
| Water | 0–20 |
| Emollient | 0–30 |
| Fragrance | 0–2.0 |
| Preservative | 0–1.5 |

Both anhydrous and hydrous gel formulations are encompassed by the present invention. Anhydrous formulations contain as essential components the two active ingredients, the dihydroxy alcohol and/or the trihydroxy alcohol, the lower alkanol and gelling agent. They may also contain other components conventionally employed in gel formulations, e.g. emollients such as isopropyl myristate, PPG-5-ceteth-20, PPG-10 methyl glucose ether, PPG-20 methyl glucose ether, PG dioctanate, methyl gluceth-10, methyl gluceth-20, isodecyl neopentanoate, glycerin, mineral oil, etc. (preferably in an amount of up to about 30%, more preferably about 5–30%), and antioxidants, e.g. ascorbyl palmitate, BHT, BHA, etc., chelating agents such as EDTA, and other preservatives such as salicylic acid, fragrances (up to about 2%), dyes, skin penetration enhancers, etc.

The preferred gel formulations of the present invention, both aqueous and anhydrous, contain an emollient component. The most preferred emollients are isopropyl myristate, PPG-5-ceteth-20, PPG-20 methyl glucose ether, or a mixture thereof.

A preferred anhydrous gel formulation of the present invention comprises sulconazole nitrate 1% and hydrocortisone 17-valerate 0.2% gel of the following composition:

| Component | Amount, % w/w |
|---|---|
| sulconazole nitrate | 1 |
| hydrocortisone 17-valerate | 0.2 |
| ethyl alcohol | 61.3 |
| propylene glycol | 25 |
| isopropyl myristate | 5 |
| hydroxypropyl cellulose | 2 |
| salicylic acid | 0.5 |
| PPG-5-ceteth-20 | 5 |

Another preferred anhydrous gel formulation is that of the formula:

| Component | Amount, % w/w |
|---|---|
| sulconazole nitrate | 1 |
| hydrocortisone 17-valerate | 0.2 |
| ethyl alcohol | 50 |
| propylene glycol | 30 |

-continued

| Component | Amount, % w/w |
| --- | --- |
| PPG-5-ceteth-20 | 17.45 |
| hydroxypropyl cellulose | 0.75 |
| salicylic acid | 0.5 |
| ascorbyl palmitate | 0.1 |

Hydrous (or aqueous) gel formulations of the present invention contain, in addition to the components described above for the anhydrous formulations, water in an amount up to about 20%, most preferably in an amount of from about 5 to 10%. In the hydrous gel formulations it is necessary that the pH of the formulation be within the range of about 3-5. This may be accomplished, if necessary, by use of conventional pharmaceutically acceptable acids or bases.

A preferred aqueous gel formulation of the present invention has the following formula:

| Component | Amount, % w/w |
| --- | --- |
| sulconazole nitrate | 1 |
| hydrocortisone 17-valerate | 0.2 |
| ethanol | 61.3 |
| propylene glycol | 20 |
| water | 10 |
| isopropyl myristate | 5 |
| hydroxypropyl cellulose | 2 |
| salicylic acid | 0.5 |

The gel-form compositions of the present invention may be formulated by the conventional mixing of the components described above. To illustrate preparation of a hydrous formulation, ethanol, propylene glycol and water are mixed together to form the co-solvent system. Salicylic acid, emollient, preservative and/or antioxidant are dissolved into the co-solvent system. Twenty-five percent of the solvent system is used to dissolve sulconazole nitrate. Another 25% of solvent is used to dissolve hydrocortisone 17-valerate. Gelling agent is added the remaining 50% of solvent and stirred vigorously for more than 45 minutes to hydrate the gel. After completion of the gelling process, sulconazole nitrate solution and hydrocortisone 17-valerate solution are added separately into the gel solution to form the final product.

The gel compositions of the present invention are clear and stable with a shelf life of two years or more at room temperature when a 10% overage of active ingredients is used.

It has been unexpectedly found that the gel formulations of the present invention also provide desirable skin penetration rates of imidazole and 17-ester steroid. For example, the skin penetration rate of 17-ester steroid in the combination product can be adjusted to the same level as exhibited by existing 17-ester steroid ointments and creams, while much higher levels of imidazole antifungal agent can be delivered as compared to the presently available imidazole solutions and creams. (see FIG. 1 and FIG. 2). This unique feature of the gel formulation enables it to provide an effective level of imidazole against fungal infection while still maintaining a safe level of 17-ester steroid. FIG. 1 demonstrates that, when compared to marketed hydrocortisone 17-valerate creams and ointments, the hydrous gel of the present invention achieves at least an equal skin penetration of the 17-ester steroid relative to such products while the anhydrous gel achieves a somewhat enhanced effect. FIG. 2 shows that, when compared to solution and cream formulations of sulconazole nitrate, both the hydrous and anhydrous gel formulations of the present invention achieve substantially increased skin penetration rates of the imidazole antifungal agent. As mentioned previously, the skin penetration rate in the gel formulations of the present invention can be controlled by the percentage of lower alkanol in the formulation, with higher alkanol concentrations giving higher skin penetration rates. We have found that the lower alkanol should be employed in the amount of from about 30-65% and the dihydroxy alcohol in an amount of from about 0-45% and/or the trihydroxy alcohol in an amount of from 0-40% for optimum stability, skin penetration effects and comfort, i.e. lack of irritation.

Topical treatment regimens according to the practice of this invention involve applying the compositions herein directly to the skin at the situs of the fungal infection. The rate of application and duration of treatment will depend upon the severity and nature of the condition, the response of a particular patient, and related factors within the sound medical judgment of an attending physician or the patient. In general, the gel formulation is applied at least daily, preferably twice or three times per day, until the eradication of the fungal infection.

The following non-limiting examples illustrate the pharmaceutical compositions of the present invention.

EXAMPLE 1

Preparation of Aqueous 1% Sulconazole Nitrate/0.2% Hydrocortisone-17-valerate Gel

| | % w/w |
| --- | --- |
| sulconazole nitrate | 1 |
| hydrocortisone 17-valerate | 0.2 |
| ethanol | 50 |
| propylene glycol | 33 |
| isopropyl myristate | 5 |
| water | 5 |
| PPG-5-ceteth-20 | 4.2 |
| hydroxypropyl cellulose | 0.9 |
| salicylic acid | 0.5 |
| ascorbyl palmitate | 0.2 |
| q.s. NaOH 1N adjust pH to 4.0 | |

Ethanol (5.1 kg), propylene glycol (3.3 kg) and isopropyl myristate (0.5 kg) were added to a suitable mixing vessel. Then, with rapid mixing 0.420 kg of PPG-5-Cetech-20 was added and the reaction mixture was mixed until uniform. With rapid mixing, 0.020 kg ascorbyl palmitate, 0.105 kg sulconazole nitrate and 0.050 kg salicylic acid were slowly added and mixing was continued until all solids were dissolved. Into a separate pre-mix vessel 0.075 kg water was added and then 0.004 kg NaOH was slowly added with mixing until the reaction mixture was uniform. To the original mixing vessel, there was then added 0.400 kg water and the NaOH solution with continued mixing for 5 to 10 minutes until a uniform consistency was achieved. The pH of the reaction mixture was determined to be 4.1. To the main vessel 0.025 kg water was added followed by 0.022 kg hydrocortisone 17-valerate. Rapid mixing was continued for about 15 minutes. Then, with rapid mixing, 0.090 kg hydroxypropyl cellulose was added and the reaction mixture was mixed rapidly for about two hours to obtain the desired gel.

| | % w/w |
|---|---|
| Example 2 | |
| sulconazole nitrate | 1 |
| hydrocortisone 17-valerate | 0.2 |
| ethanol | 50 |
| propylene glycol | 30 |
| PPG-5-Ceteth-20 | 12.3 |
| isopropyl myristate | 5 |
| hydroxypropyl cellulose | 0.9 |
| salicylic acid | 0.5 |
| ascorbyl palmitate | 0.1 |
| Example 3 | |
| sulconazole nitrate | 1 |
| hydrocortisone 17-valerate | 0.2 |
| ethanol | 35 |
| propylene glycol | 40 |
| PPG-5-Ceteth-20 | 12.3 |
| water | 5 |
| isopropyl myristate | 5 |
| hydroxypropyl cellulose | 0.9 |
| salicylic acid | 0.5 |
| ascorbyl palmitate | 0.1 |
| Example 4 | |
| miconazole nitrate | 1 |
| hydrocortisone 17-valerate | 0.2 |
| ethanol | 50 |
| propylene glycol | 30 |
| PPG-5-Ceteth-20 | 12.45 |
| isopropyl myristate | 5 |
| hydroxypropyl cellulose | 0.75 |
| salicylic acid | 0.5 |
| ascorbyl palmitate | 0.1 |
| Example 5 | |
| econazole nitrate | 1 |
| hydrocortisone 17-valerate | 0.2 |
| ethanol | 50 |
| propylene glycol | 30 |
| PPG-5-Ceteth-20 | 12.45 |
| isopropyl myristate | 5 |
| hydroxypropyl cellulose | 0.75 |
| salicylic acid | 0.5 |
| ascorbyl palmitate | 0.1 |
| Example 6 | |
| sulconazole nitrate | 1 |
| hydrocortisone 17-valerate | 0.2 |
| isopropanol | 50 |
| propylene glycol | 30 |
| PPG-5-Ceteth-20 | 12.45 |
| isopropyl myristate | 5 |
| hydroxyethyl cellulose | 0.75 |
| salicylic acid | 0.5 |
| ascorbyl palmitate | 0.1 |
| Example 7 | |
| sulconazole nitrate | 1 |
| hydrocortisone 17-valerate | 0.2 |
| ethanol | 50 |
| 2-ethyl-1,3-hexanediol | 22 |
| propylene glycol | 15 |
| isopropyl myristate | 5 |
| water | 4.99 |
| hydroxypropyl cellulose | 0.9 |
| salicylic acid | 0.5 |
| BHT | 0.2 |
| BHA | 0.2 |
| disodium EDTA | 0.01 |
| q.s. NaOH 1N adjust to pH 4.0 | |
| Example 8 | |
| sulconazole nitrate | 1 |
| hydrocortisone 17-valerate | 0.2 |
| ethanol | 50 |
| 1,2,6-hexanetriol | 27 |
| 2-ethyl-1,3-hexanediol | 7.5 |
| isopropyl myristate | 7.5 |
| PPG-20 methyl glucose ether | 5 |
| hydroxypropyl cellulose | 0.9 |
| salicylic acid | 0.5 |
| BHT | 0.2 |
| BHA | 0.2 |

REFERENCES

1. Wortzel, M. Y., H., A double-blind study comparing the superiority of a combination anti-fungal (clotrimazole/steroidal(betamethasone dipropionate)) product Cutis 30: 258 (1982).
2. Katz, H. I., Bard, J., Cole, G. W., Fischer, S., McCormick, G. E., Medansky, R. S., Nesbitt, L. T., and Rex, I. H., SCH 370 (clotrimazole-betamethasone dipropinate) cream in patients with tinea cruri or tinea corporis. Cutis, 34(2), 183–8(1984).
3. Bruice, T. C., and Schmir, G. L., Arch. Biochem. Biophys. 63: 484(1956).
4. Bruice, T. C., and Schmir, G. L., Imidazole catalysis. I. The catalysis of the hydrolysis of phenyl acetates by imidazole., J. Am. Chem., Soc., 79: 1663–9(1957).
5. Bruice, T. C., and Schmir, G. L., Imidazole catalysis. II. The reaction of substituted imidazoles with phenyl acetates in aqueous solution., J. Am. Chem. Soc., 80: 148–56(1958).
6. Bender, M. L., and Turnquest, B. W., General Basic catalysis of ester hydrolysis and its relationship to enzymatic hydrolysis., J. Am. Chem. Soc., 79: 1656–62(1957).
7. Richter Gedeon Vegy, Stable antifungal and antiinflammatory ointment, JP 76576.
8. Yip, Y. W., Po, L. W., and Irwin, W. J., Kinetics of decomposition and formulation of hydrocortisone butyrate in semi-aqueous and gel systems, J. Pharm. Sci., 72, 776–81(1983).
9. Gupta V. D., Effect of vehicles and other active ingredients on stability of hydrocortisone., J. Pharm. Sci., 67: 299(1978).
10. Hansen, J. and Bundgaard, H., Studies on the stability of corticosteroids V. The degradation pattern of hydrocortisone in aqueous solution., Int. J. Pharm., 6: 307–19(1980).

We claim:

1. A stable anhydrous gel formulation for topical administration comprising (a) a therapeutically effective amount of a mixture of an imidazole antifungal agent and a 17-ester steroid antiinflammatory agent, (b) a solvent system consisting essentially of a lower alkanol in combination with a dihydroxy alcohol or a trihydroxy alcohol or a mixture thereof and (c) an effective amount to cause gelling of hydroxypropyl cellulose or hydroxyethyl cellulose.

2. A stable anhydrous gel formulation for topical administration comprising (a) from about 0.2% to 2% by weight of an imidazole antifungal agent; (b) from about 0.01% to 2.5% by weight of a 17-ester steroid antiinflammatory agent; (c) from about 30–65% by weight of ethanol or isopropanol, or a mixture thereof; (d) from about 0–45% by weight of propylene glycol or 2-ethyl-1,3-hexanediol, or a mixture thereof; (e) from about 0–40% by weight of 1,2,6-hexanetriol and (f) from about 0.1–5% by weight of a gelling agent selected from hydroxypropyl cellulose and hydroxyethyl cellulose.

3. A gel formulation of claim 2 which also contains up to about 30% of an emollient soluble in the gel vehicle.

4. A gel formulation of claim 3 wherein the emollient is isopropyl myristate, PPG-5-ceteth-20, PG dioctanate, methyl gluceth-10, isodecyl neopentanoate, glycerin, mineral oil, methyl gluceth-20, PPG-10 methyl glucose ether, PPG-20 methyl glucose ether, or a mixture thereof.

5. A gel formulation of claim 4 wherein the emollient is isopropyl myristate, PPG-5-ceteth-20 or PPG-20 methyl glucose ether, or a mixture thereof.

6. A gel formulation of claim 2, 3, 4 or 5 which also contains an effective amount of a preservative.

7. A stable anhydrous gel formulation for topical administration having substantially the following formula:

| Component | Amount, % w/w |
| --- | --- |
| sulconazole nitrate | 1 |
| hydrocortisone 17-valerate | 0.2 |
| ethanol | 61.2 |
| propylene glycol | 25 |
| isopropyl myristate | 5 |
| hydroxypropyl cellulose | 2 |
| salicylic acid | 0.5 |

-continued

| Component | Amount, % w/w |
| --- | --- |
| PPG-5-ceteth-20 | 5 |
| ascorbyl palmitate | 0.1 |

8. A stable anhydrous gel formulation for topical administration having substantially the following formula:

| Component | Amount, % w/w |
| --- | --- |
| sulconazole nitrate | 1 |
| hydrocortisone 17-valerate | 0.2 |
| ethanol | 50 |
| propylene glycol | 30 |
| PPG-5-ceteth-20 | 17.45 |
| hydroxypropyl cellulose | 0.75 |
| salicylic acid | 0.5 |
| ascorbyl palmitate | 0.1 |

* * * * *